US012558231B2

(12) United States Patent
Weiman et al.

(10) Patent No.: US 12,558,231 B2
(45) Date of Patent: *Feb. 24, 2026

(54) PEDICLE-BASED INTRADISCAL FIXATION

(71) Applicant: GLOBUS MEDICAL, INC., Audubon, PA (US)

(72) Inventors: Mark Weiman, Downingtown, PA (US); Myles Sullivan, Philadelphia, PA (US); Carly Taubenkraut, Perkasie, PA (US); Chad Glerum, Pennsburg, PA (US); Corbett McLaughlin, Bryn Mawr, PA (US)

(73) Assignee: Globus Medical Inc., Audubon, PA (US)

( * ) Notice: Subject to any disclaimer, the term of this patent is extended or adjusted under 35 U.S.C. 154(b) by 132 days.

This patent is subject to a terminal disclaimer.

(21) Appl. No.: 18/541,203

(22) Filed: Dec. 15, 2023

(65) Prior Publication Data

US 2024/0138998 A1 May 2, 2024

Related U.S. Application Data

(63) Continuation of application No. 17/718,900, filed on Apr. 12, 2022, now Pat. No. 11,871,964, which is a
(Continued)

(51) Int. Cl.
*A61B 17/70* (2006.01)
*A61F 2/30* (2006.01)
*A61F 2/44* (2006.01)

(52) U.S. Cl.
CPC .......... *A61F 2/446* (2013.01); *A61B 17/7011* (2013.01); *A61F 2/30749* (2013.01);
(Continued)

(58) Field of Classification Search
CPC ................. A61F 2/446; A61F 2/30749; A61F 2002/30092; A61F 2002/30235;
(Continued)

(56) References Cited

U.S. PATENT DOCUMENTS

| | | | | |
|---|---|---|---|---|
| 5,549,609 A | * | 8/1996 | Frankel | A61B 17/1739 |
| | | | | 606/64 |
| 5,810,820 A | * | 9/1998 | Santori | A61B 17/744 |
| | | | | 606/63 |

(Continued)

FOREIGN PATENT DOCUMENTS

EP 2845553 A1 3/2015

*Primary Examiner* — Eduardo C Robert
*Assistant Examiner* — David C Comstock

(57) ABSTRACT

Pedicle-based intradiscal fixation devices, systems, instruments, and methods thereof. A pedicle-based intradiscal implant for stabilizing an inferior vertebra and a superior vertebra may include a bendable rod configured to engage bone, a bone fastener defining a channel for receiving the bendable rod, and a locking cap for securing the bone fastener and the bendable rod. The implant may be positioned through a pedicle of an inferior vertebra and the bendable rod may be deployable into the vertebral body of the inferior vertebra, through the disc space, and into the vertebral body of the superior vertebra to stabilize the spine.

20 Claims, 17 Drawing Sheets

Related U.S. Application Data continuation of application No. 17/718,871, filed on Apr. 12, 2022, now Pat. No. 11,872,140.

(52) U.S. Cl.
CPC .............. *A61F 2002/30092* (2013.01); *A61F 2002/30235* (2013.01); *A61F 2002/30507* (2013.01); *A61F 2002/3085* (2013.01); *A61F 2310/00023* (2013.01)

(58) Field of Classification Search
CPC .... A61F 2002/30507; A61F 2002/3085; A61F 2310/00023
USPC ..... 623/17.11; 606/246, 254, 255, 261, 262, 606/264, 265, 276, 300, 305, 308, 310, 606/319, 328
See application file for complete search history.

(56) References Cited

U.S. PATENT DOCUMENTS

| | | | | |
|---|---|---|---|---|
| 6,558,388 | B1 * | 5/2003 | Bartsch | A61B 17/7225 |
| | | | | 606/62 |
| 10,258,329 | B2 * | 4/2019 | Moskowitz | A61B 17/8685 |
| 10,499,969 | B2 * | 12/2019 | McGirt | A61B 17/7032 |
| 11,872,140 | B2 * | 1/2024 | Weiman | A61B 17/70 |
| 2005/0010216 | A1 * | 1/2005 | Gradel | A61B 17/7041 |
| | | | | 606/264 |
| 2010/0057141 | A1 | 3/2010 | Abdelgany et al. | |
| 2010/0160967 | A1 | 6/2010 | Capozzoli | |
| 2013/0150851 | A1 * | 6/2013 | Nardini | A61B 17/7233 |
| | | | | 606/64 |
| 2016/0310190 | A1 | 10/2016 | Gonzalez et al. | |
| 2019/0125409 | A1 | 5/2019 | Bohl | |
| 2022/0133491 | A1 * | 5/2022 | Glerum | A61B 17/8625 |
| | | | | 606/279 |

* cited by examiner

PEDICLE-BASED INTRADISCAL FIXATION

CROSS-REFERENCE TO RELATED APPLICATIONS

This application is a continuation application of U.S. patent application Ser. No. 17/718,900, filed on Apr. 12, 2022 (published as U.S. Pat. Pub. No. 2023-0320757), which is a continuation application of U.S. patent application Ser. No. 17/718,871, filed on Apr. 12, 2022 (published as U.S. Pat. Pub. No. 2023-0320867), all of which are incorporated in their entireties herein for all purposes.

FIELD OF THE INVENTION

The present disclosure relates to surgical devices, and more particularly, to pedicle-based intradiscal fixation devices and associated methods.

BACKGROUND OF THE INVENTION

Common procedures for handling pain associated with intervertebral discs that have become degenerated due to various factors such as trauma or aging may include the use of pedicle screw fixation and/or intervertebral fusion for fusing one or more adjacent vertebral bodies. Generally, bilateral pedicle screw fixation, for example, with a rod construct, may be used to treat degenerative disc disease and a multitude of other spine pathologies as a standard of treatment to stabilize two or more adjacent vertebral bodies, for example, as an adjunct to spinal fusion.

Unfortunately, a number of iatrogenic pathologies are associated with pedicle screw fixation including, but not limited to, misplacement of screws, muscle/ligamentous disruption during insertion, adjacent segment disease due to superior adjacent facet violation by the inferior pedicle screw construct, increased procedural time, and/or instrumentation failure. There exists a clinical need for a fixation system and method that reduces the iatrogenic effects of a bilateral pedicle screw construct from a posterior approach while stabilizing two adjacent vertebral bodies that may be used as an adjunct to spinal fusion.

SUMMARY OF THE INVENTION

In accordance with the application, pedicle-based intradiscal devices, systems, and methods are provided. In particular, pedicle-based intradiscal fixation may be used as one or more standalone devices or may be used in conjunction with an interbody fixation device. The method of fixation may include inserting the device through the pedicle of an inferior vertebra, into the vertebral body of the inferior vertebra, through the disc space, and securing the device to the vertebral body of the adjacent superior vertebra. The pedicle-based intradiscal fixation devices and methods described herein may improve access-related morbidity while providing sufficient stabilization force for spinal fusion.

According to one embodiment, a pedicle-based intradiscal implant for stabilizing an inferior vertebra and a superior vertebra includes a bendable rod, a bone fastener, and a locking cap. The bendable rod extends from a proximal end having an outer threaded portion to a distal end with a sharp tip configured to engage bone. The bone fastener has a threaded screw head and a shaft extending along a central longitudinal axis. The bone fastener defines a channel for receiving the bendable rod. The channel has a straight portion extending along the central longitudinal axis and a curved portion with an exit through a sidewall of the shaft. The locking cap includes an internally threaded seat for engaging with the screw head of the bone fastener and a central protrusion defining a cavity for receiving the proximal end of the bendable rod.

The pedicle-based intradiscal implant may include one or more of the following features. The locking cap may have a cylindrical body defining a drive recess opposite to the internally threaded seat. The cavity in the central protrusion of the locking cap may be non-threaded and configured to push the rod forward, thereby compressing the rod securely. Alternatively, the cavity in the central protrusion of the locking cap may be threaded and configured to mate with the outer threaded portion of the bendable rod, thereby pulling the rod backward to secure the rod. The straight portion of the channel may extend through the screw head and along the shaft toward a distal end of the bone fastener and the curved portion of the channel may be located near the distal end of the bone fastener. The bendable rod may be flexible such that the rod has a straight configuration and is bendable into a curved configuration. In the curved configuration, the bendable rod may have a straight portion and a curved portion where the rod is curved in an arc up to 180°. The bendable rod may be formed of a shape-memory material, such as nitinol. A distal portion of the bendable rod may have a polygonal cross-section with planar faces and a proximal portion of the bendable rod may have a cylindrical shape. The bone fastener may be a pedicle screw with a proximal end including a recess configured to receive an instrument for inserting the pedicle screw and a distal end with a tip configured to be inserted into the pedicle of the inferior vertebra.

According to another embodiment, a hybrid implant suitable for use with a revision procedure may include a bendable rod configured to engage bone, a bone fastener, a locking cap, and a tulip head coupled to the locking cap. The bone fastener has a screw head and a shaft. The bone fastener defines a channel for receiving the bendable rod. The channel has a straight portion extending through the screw head and along a portion of the shaft and a curved portion with an exit through a sidewall of the shaft. The locking cap defines an internal seat for engaging with the screw head of the bone fastener and a central protrusion defining a cavity for receiving one end of the bendable rod. The tulip head has a body with a pair of opposed arms defining a rod slot sized and configured to accept a spinal rod.

The hybrid implant may include one or more of the following features. The tulip head may be integrally coupled to the locking cap with a rigid arm. The tulip head may be offset laterally to the locking cap. The rod slot of the tulip head may be aligned in parallel to the bendable rod. The screw head may be externally threaded and the internal seat of the locking cap may be internally threaded to thereby threadedly interface with the screw head.

According to yet another embodiment, a method for stabilizing an inferior vertebra and a superior vertebra may include one or more of the following steps in any suitable order: (1) posteriorly accessing a spine of a patient; (2) inserting a fastener having a head and a shaft into a pedicle of the inferior vertebra and into a vertebral body of the inferior vertebra; (3) moving a rod through a channel in the fastener such that a distal portion of the rod curves through the channel and outside the fastener into the vertebral body of the inferior pedicle, through a disc space, and into a vertebral body of the superior vertebra; and (4) threading a locking cap onto the head of the fastener and into engagement with the rod to thereby secure the positioning of the fastener and the rod. The fastener and rod may be deployed simultaneously or the fastener may be deployed first and the rod subsequently. The method may include, before moving the rod through the channel in the fastener, attaching an instrument to a proximal end of the rod with a threaded interface. The method may include, before moving the rod through the channel in the fastener, straightening the rod. The method may include installing two implants including a first fastener and first rod deployed from an ipsilateral pedicle of the inferior vertebra, and a second fastener and second rod deployed through the contralateral pedicle of the inferior vertebra.

Also provided are kits including pedicle-based intradiscal fixation devices of varying types and sizes, interbody fusion devices of varying types and sizes, rods, fasteners or anchors, k-wires, insertion tools and other instruments, and other components for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

Bilateral pedicle screw fixation has been used to treat degenerative disc disease and other spine pathologies. However, a number of iatrogenic pathologies are associated with pedicle screw fixation. Thus, there is a need for a fixation method that reduces the iatrogenic effects of a bilateral pedicle screw construct from a posterior approach while stabilizing the two adjacent vertebral bodies. According to one embodiment, an inferior pedicle-based intradiscal fixation method may be used in a standalone method or in conjunction with an interbody fixation device. The system may improve access-related morbidity by reducing procedural steps, minimizing soft tissue disruption, and ultimately eliminating violation of the superior facet joint to reduce the risk of adjacent segment disease all while providing improved stability in conjunction with spinal fusion devices. Accordingly, embodiments of the present application are generally directed to devices, systems, and methods for pedicle-based intradiscal fixation of two adjacent vertebrae. The terms device, fixation device, and implant may be used interchangeably herein.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments and modifications thereof are contemplated as falling within the scope of this disclosure and equivalents thereto.

Figure 1:
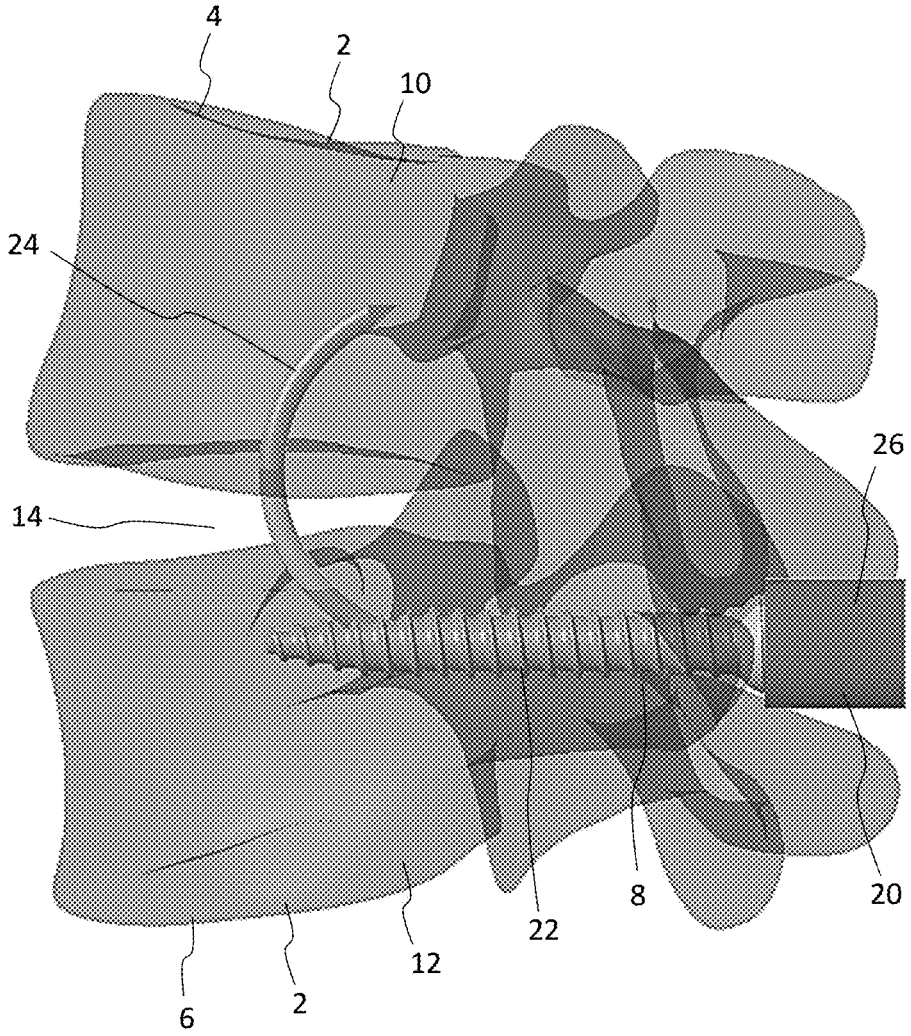
FIG. 1 is a sagittal view of two vertebrae with a pedicle-based intradiscal fixation implant implanted through the pedicle of the inferior vertebra and engaged with the vertebral body of the superior vertebra according to one embodiment.
Figure 2:
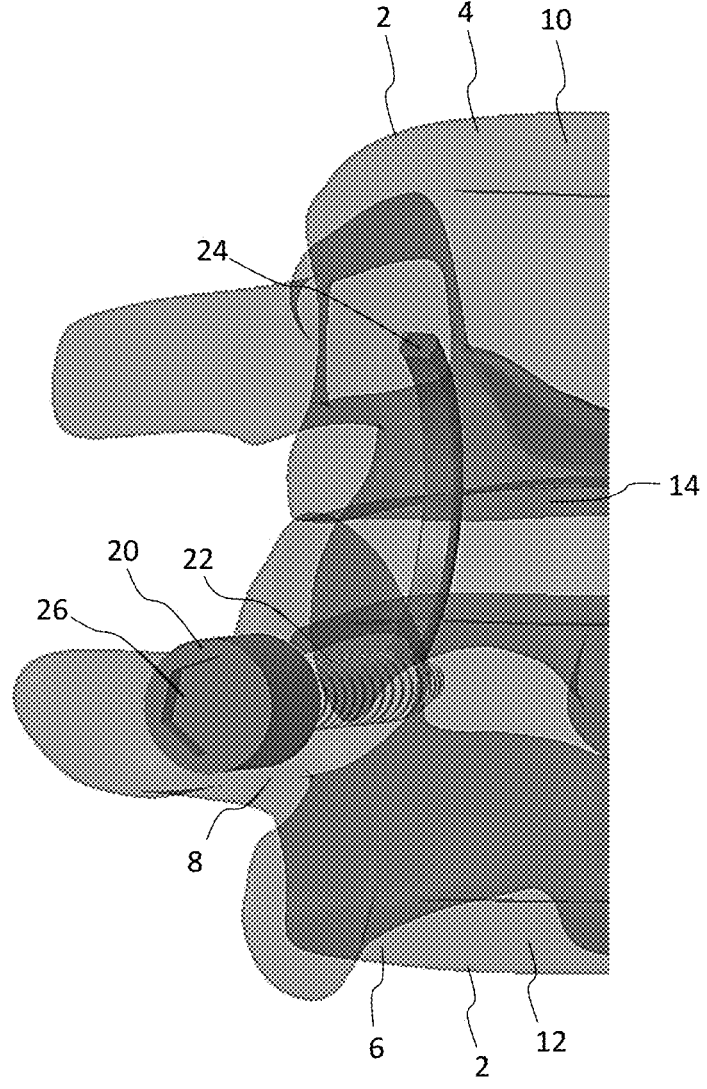
FIG. 2 is a posterior view of the vertebrae and pedicle-based intradiscal fixation device of FIG. 1.
Figure 3:
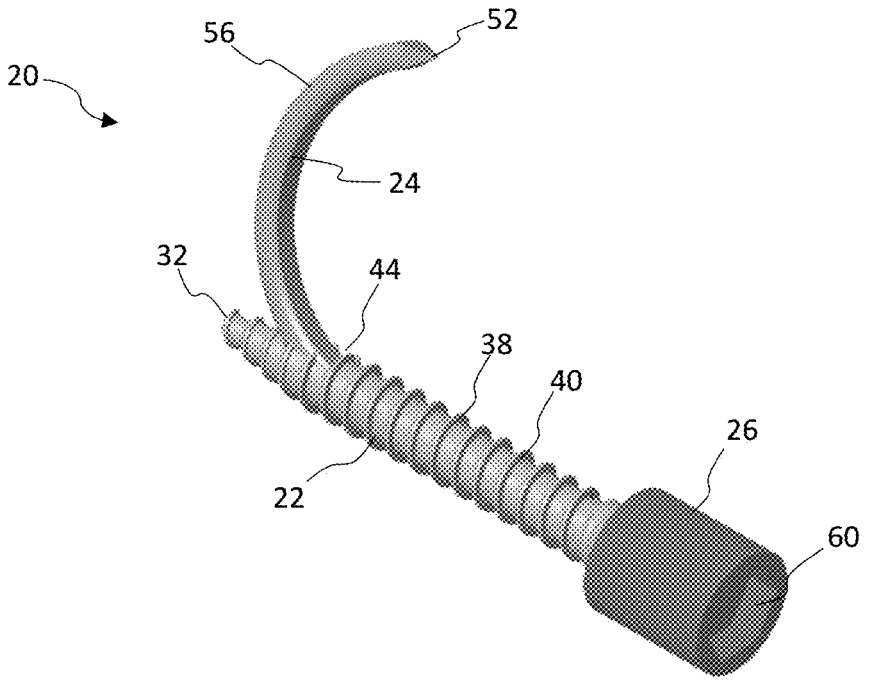
FIG. 3 is a perspective view of the pedicle-based intradiscal fixation device of FIG. 1 including a bone fastener, curved rod, and locking cap.
Figure 4:
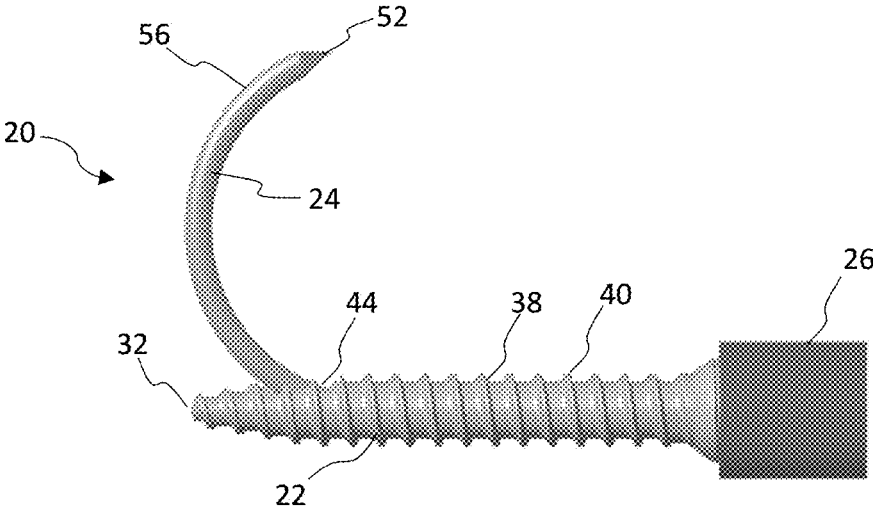
FIG. 4 is a side view of the pedicle-based intradiscal fixation device of FIG. 3.

Referring now to FIGS. 1 and 2, a pedicle-based intradiscal fixation device 20 according to one embodiment is shown implanted into two adjacent vertebrae 2, namely, a superior vertebra 4 and an inferior vertebra 6. The method of fixation may include, for example, accessing the spine from the posterior and inserting the device 20 into the pedicle 8 of the inferior vertebra 6. If necessary, bone may be removed from the inferior pedicle 8 and/or the vertebral body 12 of the inferior vertebra 6 in order to facilitate placement of the device 20. The device 20 may be further advanced into the vertebral body 12 of the inferior vertebra 6. The location and orientation of the device 20 may be selected by a surgeon. The device 20 may be further configured to be inserted and secured to the vertebral body 10 of the adjacent superior vertebra 4. Thus, the device 20 may traverse the disc and/or disc space 14 between the two vertebrae 2. In this manner, the device 20 may be configured to be implanted into both vertebrae 2 from a posterior approach, thereby allowing for fusion of the adjacent vertebrae 2. One or more pedicle-based devices 20 may be used alone or in conjunction with an interbody fusion device. Although the method is shown with respect to a single inferior pedicle 8, it will be appreciated that the other inferior pedicle may also receive the same or a similar device. It will also be appreciated that the same or similar devices may also be used on adjacent or other levels.

Figure 5:
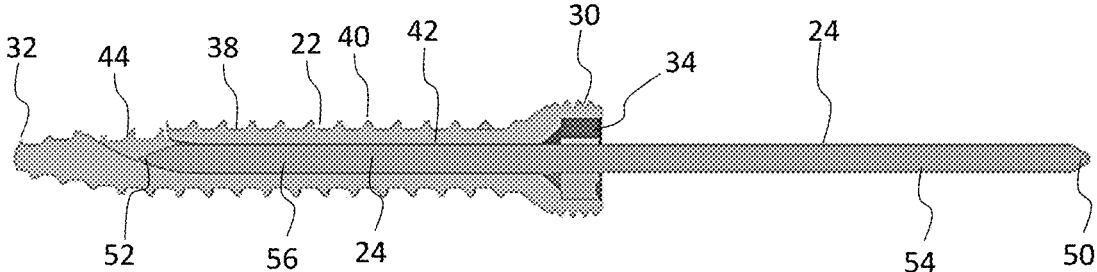
FIG. 5 shows a cross-sectional view of the rod in a straight orientation inserted into the bone fastener according to one embodiment.
Figure 6:
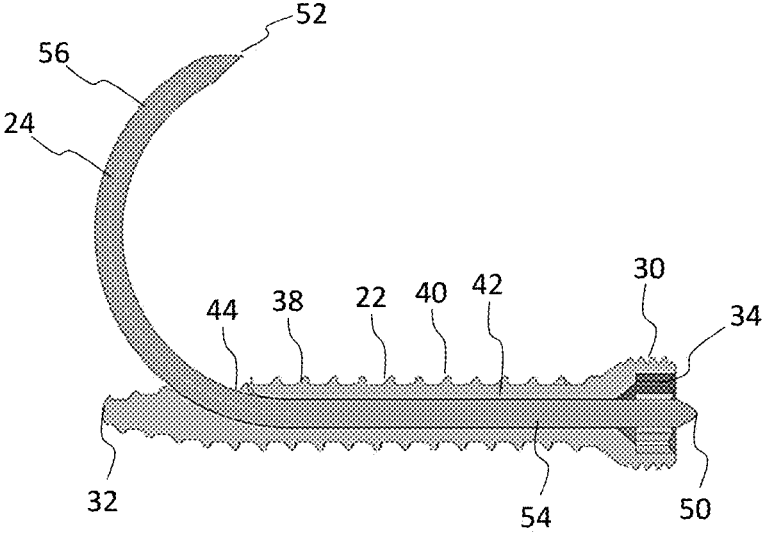
FIG. 6 shows a cross-sectional view of the rod in a curved orientation positioned through the bone fastener according to one embodiment.
Figure 7:
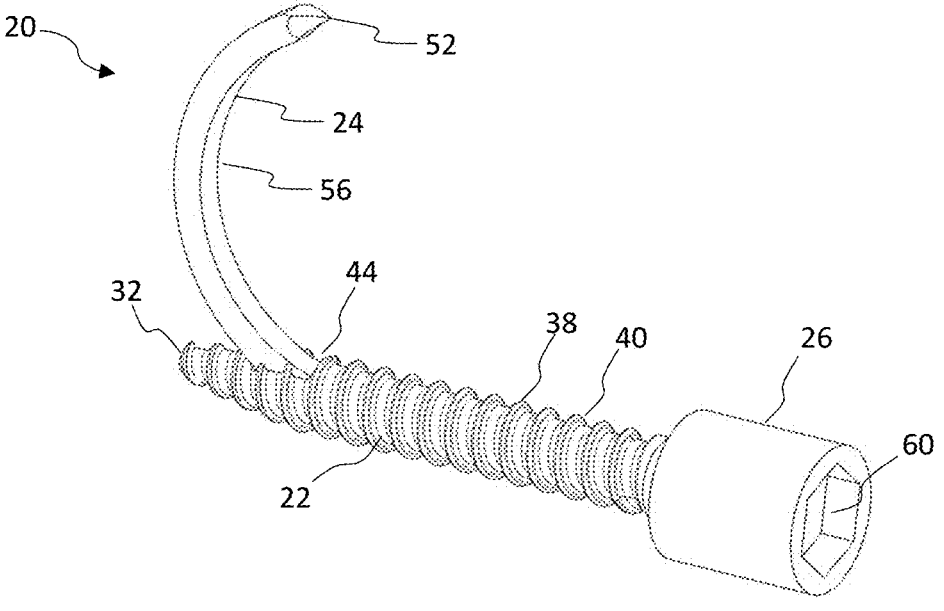
FIG. 7 is a perspective view of the pedicle-based intradiscal fixation device with the curved rod protruding from the bone fastener and the locking cap securing the curved rod according to one embodiment.
Figure 8:
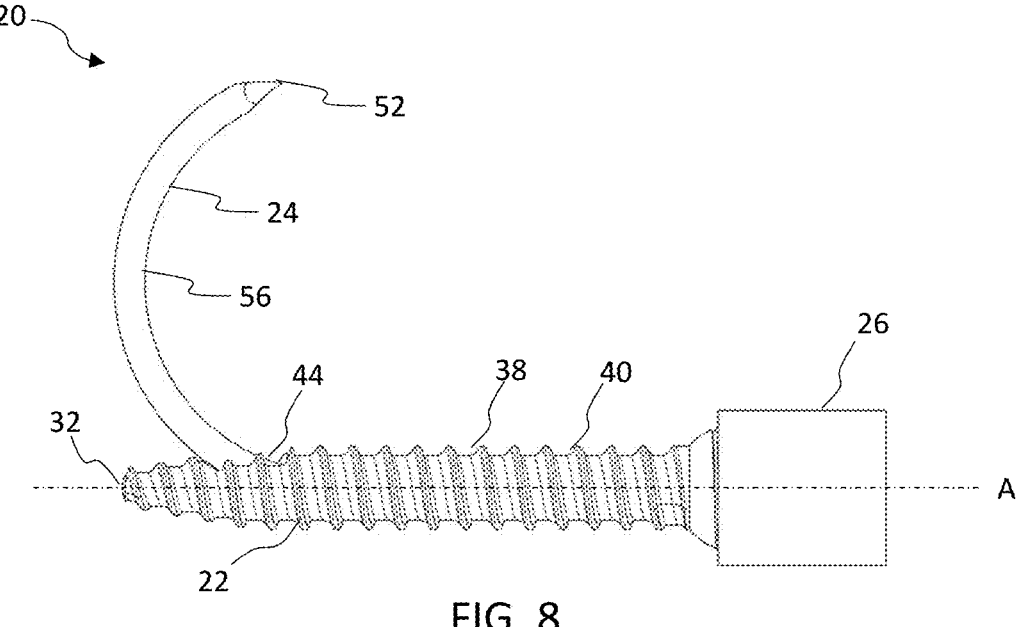
FIG. 8 is a side view of the pedicle-based intradiscal fixation device of FIG. 7.

Turning now to FIGS. 3-8, the pedicle-based intradiscal fixation implant 20 is shown in more detail. The pedicle-based fixation implant 20 may include three biocompatible components: a bone fastener 22, a rod 24, and a locking cap 26. As best seen in FIGS. 5 and 6, the bone fastener 22 includes a cannulated path 42 for the rod 24 to follow. As shown in FIG. 5, the rod 24 has a straight configuration when the rod 24 is first inserted into the bone fastener 22. The cannulated path 42 extends along the length of the fastener 22 and curves to emerge from the sidewall of the shaft 38 of the fastener. As shown in FIG. 6, when the rod 24 is fully deployed through the bone fastener 22, the rod 24 curves and protrudes outside the fastener 22. The curved portion of the rod 24 is configured to be secured through the inferior vertebral body 6, the disc space 14, and the superior vertebral body 4.

Figure 9:
FIG. 9 is a perspective view of the cannulated bone fastener according to one embodiment.
Figure 9:
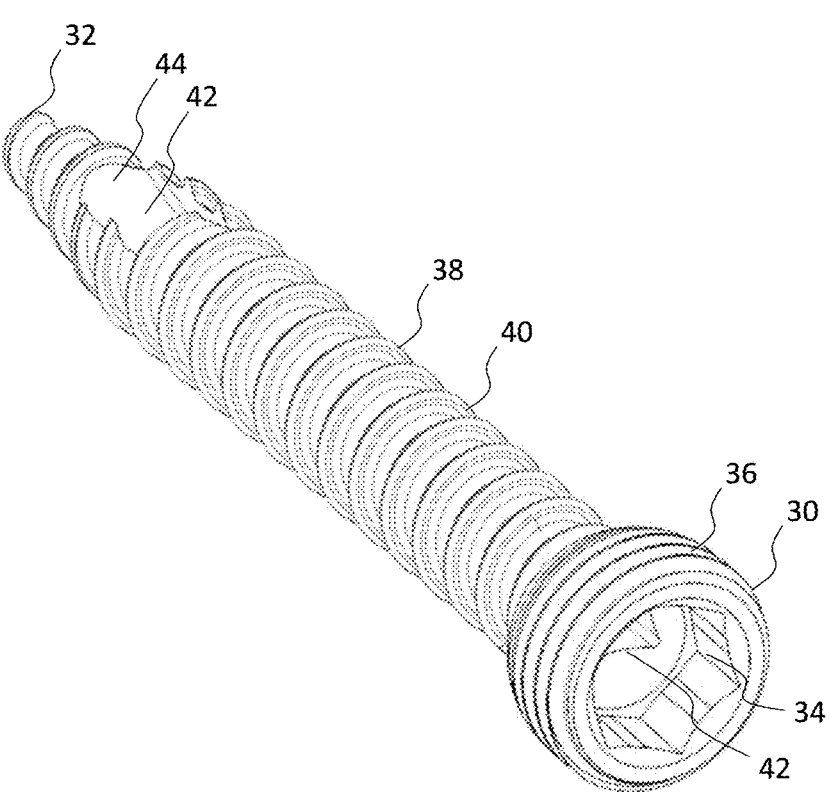
Figure 11:
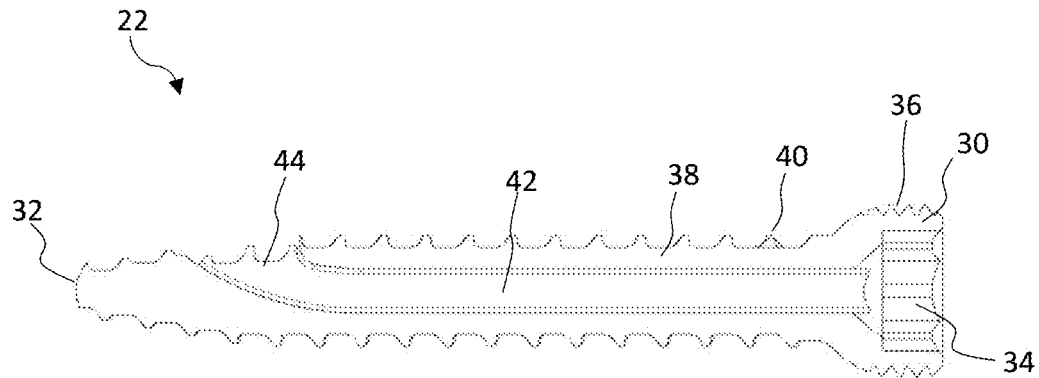
FIG. 11 is a cross-sectional view of the cannulated bone fastener according to one embodiment.

Referring now to FIGS. 9 and 11, the bone fastener 22 may be a screw, such as a pedicle screw, that extends from a proximal end with a screw head 30 to a distal end with a tip 32. The bone fastener 22 extends along a central longitudinal axis A between the proximal and distal ends. The screw head 30 may define a drive recess 34 (e.g., a female hexagonal recess or other suitable shape) that can be engaged by a screw-driving instrument or other device. The screw head 30 may be enlarged relative to the diameter of the shaft 38. The screw head 30 may have any suitable shape. In the embodiment shown, the screw head 30 has a curved or spherical surface that is threaded 36 around its periphery and configured to engage with locking cap 26. The threaded portion 36 of the screw head 30 is configured to threadedly interface with the seat 62 of the locking cap 26. It will be appreciated that the screw head 30 may be ribbed, roughened, or otherwise configured to mate with the locking cap 26.

The screw 22 has a shaft 38 with a plurality of threads 40 configured to engage bone. It will be appreciated that the threads 40 may have a number of different features to improve insertion and/or attachment to bone, such as lead(s), thread pitch, thread angle, shaft diameter to thread diameter, overall shaft shape, and the like. It is also contemplated that the threaded shaft 38 could be substituted with another suitable bone fastener, such as an anchor, clamp, or the like configured to engage bone. The shaft 38 terminates distally at tip 32. The distal tip 32 may be blunt, pointed, sharpened, or otherwise configured for insertion into bone.

The bone fastener 22 is cannulated and defines a hollow body for receiving and guiding the rod 24. The cannulated path or channel 42 extends from recess 34 in screw head 30, through the shaft 38, and through the sidewall of the shaft 38. The channel 42 has a straight portion extending along the central longitudinal axis A from the proximal end a distance toward the distal tip 32. As the channel 42 nears the distal tip 32, the channel 42 has a curved portion with an exit 44 through the outer wall of the shaft 38. In this manner, the channel 42 does not extend the entire length of the fastener 22 and does not exit the distal tip 32. The curve of the channel 42 may include a minor arc with an acute angle less than 90°. The channel 42 may have a smooth inner surface along its length. The smooth curvature may help to guide the rod 24 through the fastener 22, such that the rod 24 protrudes from the side of the shaft 38 and the rod 24 curves outside the fastener 22.

The bone fastener 22 may be comprised of one or more biocompatible materials. For example, the bone fastener 22 may be made from a metal, such as titanium, stainless steel, cobalt chrome, carbon composite, or suitable alloys (such as TAV). These materials may be machined, such as via CNC machining, constructed from additive manufacturing, such as three-dimensional (3D) printing, subtractive manufacturing, or hybrid manufacturing processes. In an exemplary embodiment, the bone fastener 22 is constructed via 3D printing with titanium. 3D printing may allow for more liberty with design as compared with traditionally accepted machining and the geometry of the screw can be unique and streamline workflow. Although the materials described herein are exemplified, it will be appreciated that any suitable materials and construction may be selected.

Figure 10:
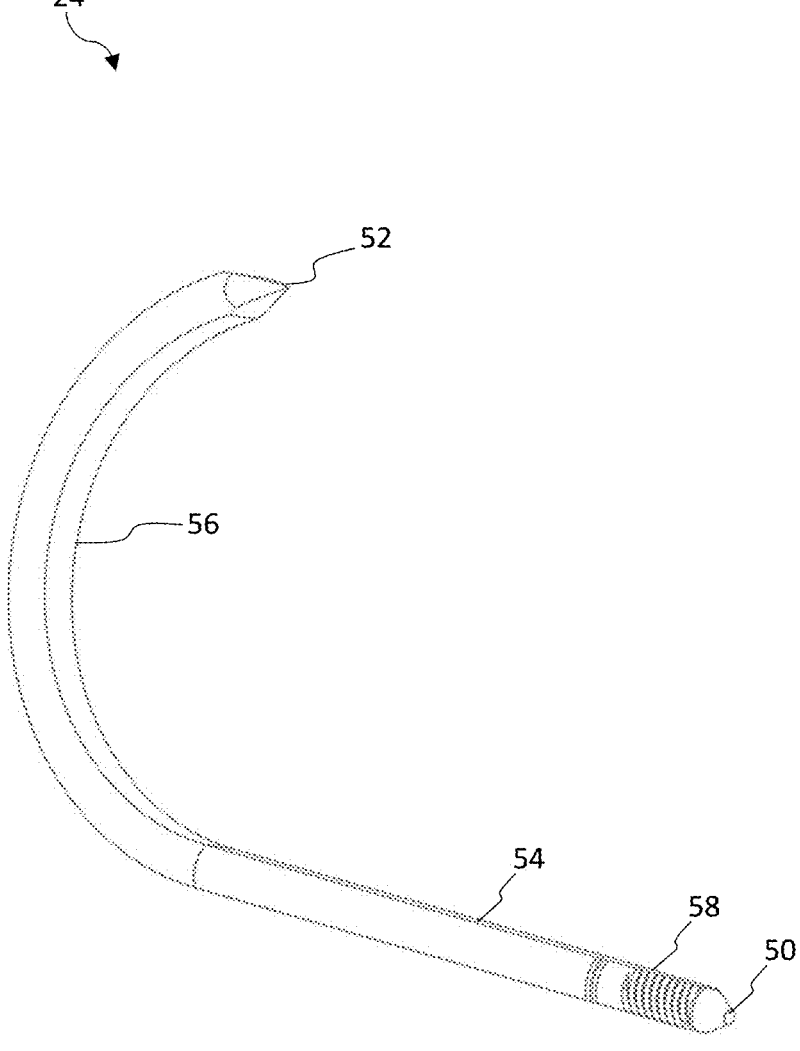
FIG. 10 is a perspective view of the curved rod according to one embodiment.

With emphasis on FIG. 10, the bendable rod 24 includes a proximal end 50 configured to mate with the locking cap 26 and a distal end 52 configured to engage bone. The rod 24 may be composed of nitinol or other shape-memory material, which allows the rod 24 to bend into a curved state upon deployment. The properties of a shape-memory material may allow for the rod 24 to be drawn into the straight configuration from its natural curved state. In its relaxed state, the rod 24 may have a curve or bend up to 180°, for example, relative to its straight configuration. The super elastic properties of nitinol allow the low profile configuration shown in FIG. 5 to be loaded straight into the fastener 22. The nitinol rod 24 may be heat treated to shape set a curvature with a defined bend radius, termination angle, and tip geometry suitable for purchasing the superior vertebra 2 when fully deployed.

The bendable rod 24 may include a proximal portion 54 and distal portion 56 with different cross-sectional shapes taken perpendicular to the length of the rod 24. Even with different cross-sections, the bendable rod 24 may have generally the same diameter along its length. The distal portion 56 of the body of the nitinol rod 24 may have a polygonal cross-section with planar faces. For example, the distal portion 56 of the body may have a generally quadrilateral cross-sectional shape, such as a square. The distal end 52 may include a pointed or sharp tip (e.g., pyramidal) configured to pierce bone. In its relaxed state, the distal portion 56 of the nitinol rod 24 may have a curve or arc with a semi-circle with an angle of about 180° or a curve or minor arc with an acute angle up to 180°. The proximal portion 54 of the rod 24 may include a generally rounded or cylindrical shape and the proximal end 50 may terminate with a conical shape. The proximal portion 54 of the rod 24 may generally retain the straight configuration even when the distal portion 56 bends about the pre-defined bend radius. The proximal portion 54 may include a threaded portion 58 near the proximal end 50, which may be configured to mate with the locking cap 26.

The locking cap 26 may include a generally cylindrical body configured to secure the rod 24 in place and/or to the fastener 22. The locking cap 26 may define a drive recess 60 at its proximal end. The drive recess 60 may be a female hexagonal recess or other suitable shape. The drive recess 60 may be engaged by a driving instrument or other device to rotate and secure the cap 26 to the screw head 30 of the fastener 22. The locking cap 26 defines a cavity or seat 62 opposite to the drive recess 60 configured to receive the screw head 30 of the bone fastener 22. The seat 62 may include a plurality of internal threads 64 configured to mate with corresponding threads 36 on the outside of the screw head 30, thereby threadedly securing the locking cap 26 to the fastener 22. It will be appreciated that the locking cap seat 62 may be ribbed, roughened, or otherwise configured to mate with the screw head 30. The locking cap 26 may be constructed of the same or similar biocompatible materials as described for the bone fastener 22.

Figure 17:
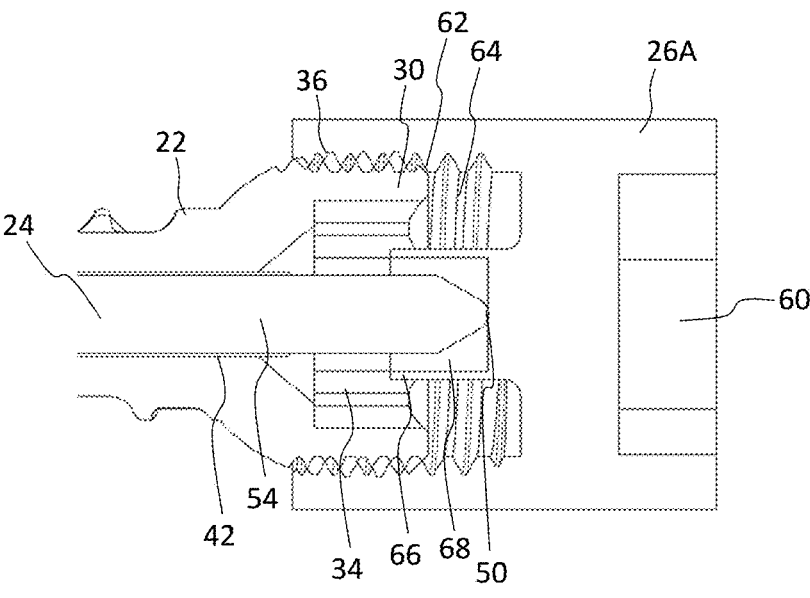
FIG. 17 shows a close up cross-sectional view of one embodiment of a locking cap for securing the rod.
Figure 18:
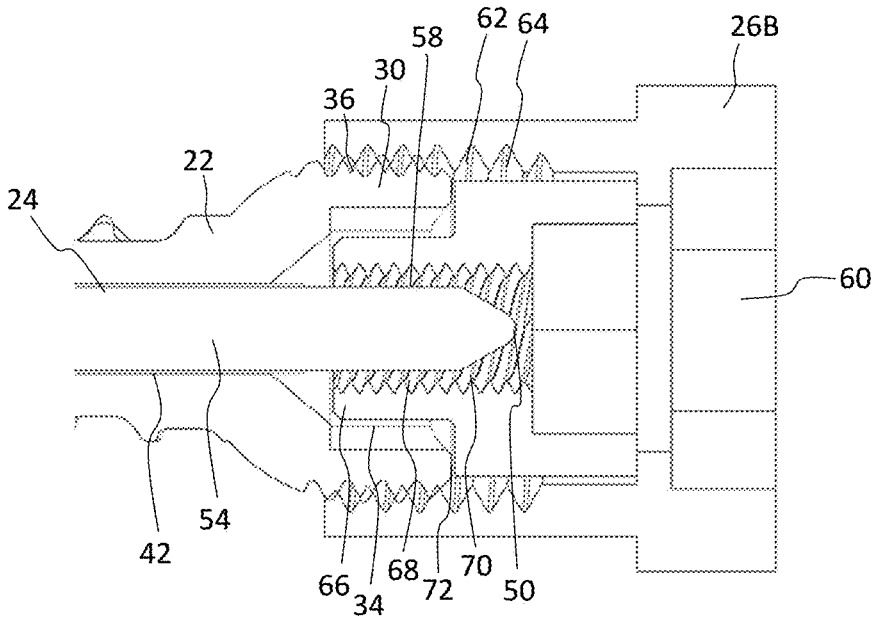
FIG. 18 shows a close up cross-sectional view of another embodiment of a locking cap for securing the rod.

With emphasis on FIGS. 17 and 18, the locking cap 26 may engage with the proximal end 50 of the rod 24, thereby securing the rod 24 in the construct. In the embodiment shown in FIG. 17, the locking cap 26A pushes the curved nitinol rod 24 slightly forward or distally to compress the rod 24 securely. For example, the locking cap seat 62 may define a central protrusion 66 with a cavity 68 for receiving the proximal end 50 of the rod 24. The central protrusion 66 may partially enter into the drive recess 34 of the screw head 30. The central protrusion 66 and cavity 68 may be aligned with the proximal portion 54 of the rod 24 along the central longitudinal axis A of the implant 20. When the locking cap 26 is threadedly secured to the screw head 30, the rod 24 seats in cavity 68 such that the proximal end 50 abuts a bottom surface of the cavity 68. In this manner, the locking cap 26A pushes the rod 24 distally, thereby compressing the rod 24.

Alternatively, in the embodiment shown in FIG. 18, the locking cap 26B is threadedly engaged with the rod 24 to pull the rod 24 back slightly in tension to secure it. In this manner, the locking cap 26B can engage threads 36, 58 on both the pedicle screw 22 and the curved nitinol rod 24, which tightly secures their positioning and interface. In this embodiment, the cavity 68 includes a plurality of threads 70 configured to interface with corresponding threads 58 on the proximal portion 54 of the rod 24. The central protrusion 66 may fully enter into the drive recess 34 of the screw head 30 such that the protrusion 66 bottoms out inside recess 34. A shoulder 72 of the protrusion 66 may be configured to abut and engage the top surface of the screw head 30, thereby allowing for the threaded connection to pull the rod 24 back proximally, thereby securing the rod 24 to the locking cap 26B.

Figure 12:
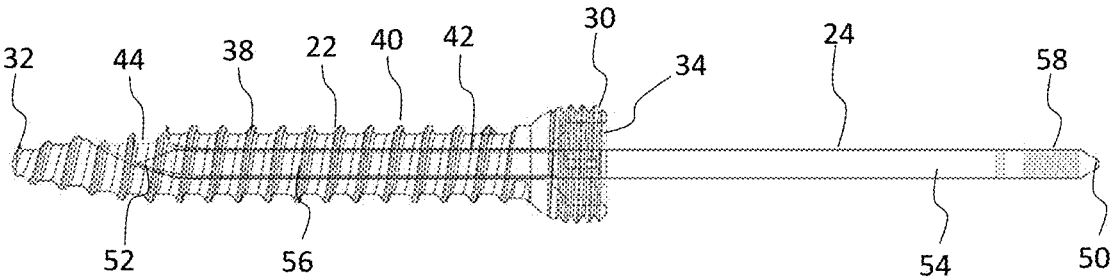
FIG. 12 shows a side view with overlaid cross-sectional view of the cannulated bone fastener and the rod in a straightened orientation according to one embodiment.
Figure 13:
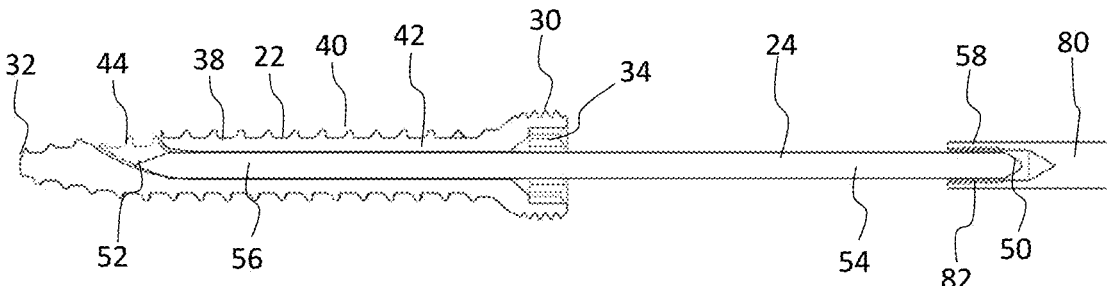
FIG. 13 shows a cross-sectional view of the cannulated bone fastener and an instrument positioning the straightened rod into the bone fastener according to one embodiment.

With further emphasis of FIGS. 12-16, a method of installing and assembling the implant 20 is shown according to one embodiment. As shown in FIG. 12, the rod 24 is straightened and inserted into the channel 42 through fastener 22. FIG. 13 shows an instrument 80 coupled to the proximal end 50 of the straightened rod 24. The instrument 80 may have an inner threaded channel 82 configured to temporarily attach the rod 24 to the instrument. It will be appreciated that any suitable attachment may be used to secure the rod 24 to the insertion instrument 80. Prior to insertion and deployment, the instrumentation 80 may capture the proximal threading 58 of the curved nitinol rod 24 and draw the rod 24 back straight and then into the body of the screw 22. The screw 22 can be driven forward safely while the deformed nitinol rod 24 is flexed straight inside its core. The super elasticity of nitinol allows for the material to be drawn into the straight configuration from its naturally curved state and allows the rod 24 to later return to its curved state once fully deployed.

Figure 14:
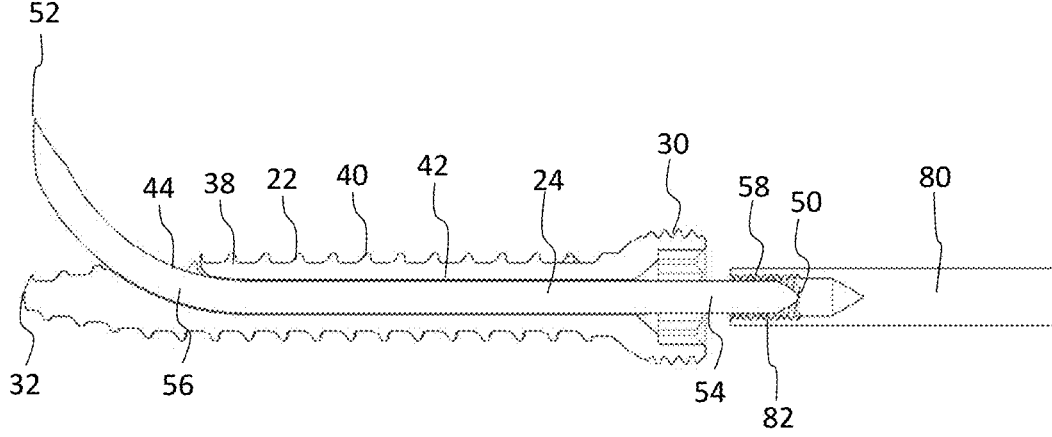
FIG. 14 shows the rod moving through the bone fastener via the instrument and the rod beginning to bend at the distal end according to one embodiment.
Figure 15:
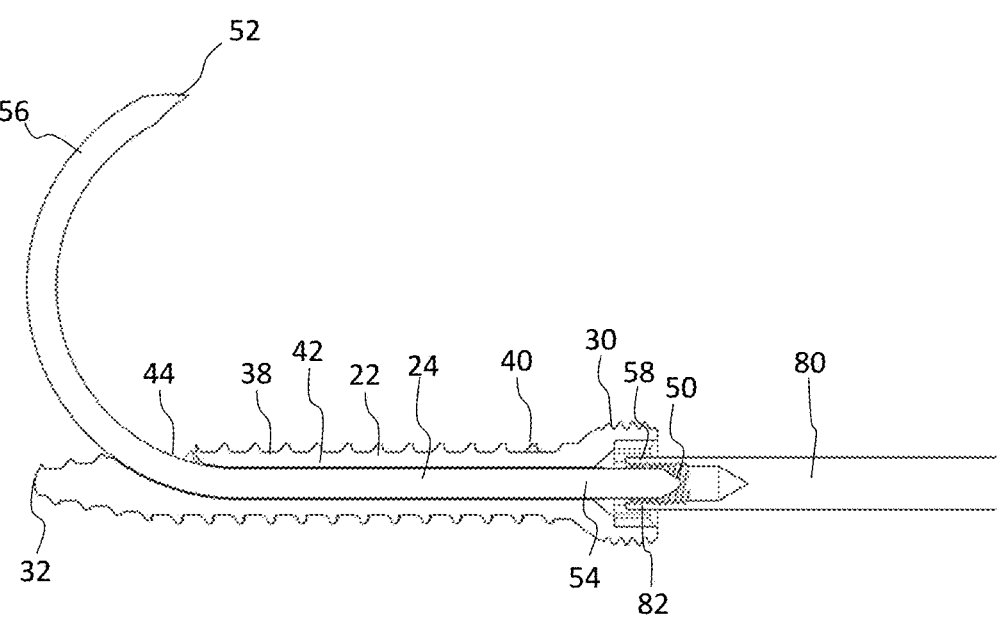
FIG. 15 shows the rod fully inserted into the bone fastener via the instrument and the rod in a curved orientation according to one embodiment.
Figure 16:
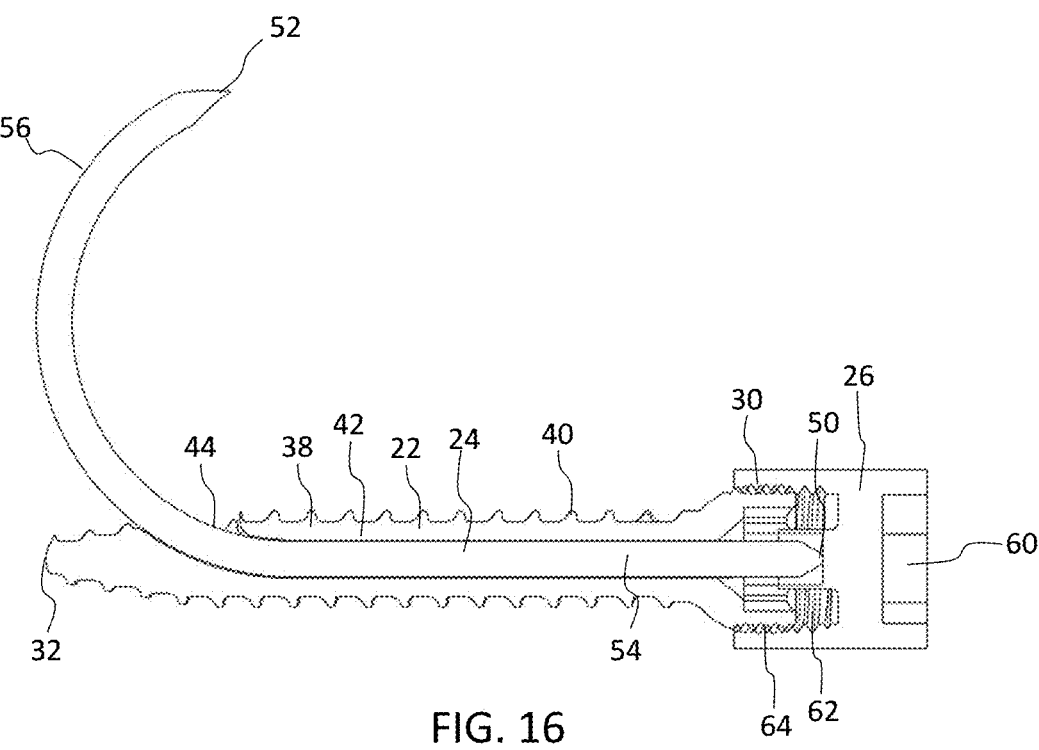
FIG. 16 shows the final construct including the bone fastener, curved rod, and a locking cap securing the rod therein according to one embodiment.

Once the screw 22 is inserted to the correct depth and orientation in accordance with pre-operative planning, the deformed nitinol rod 24 can be impacted or driven forward through the screw 22. As shown in FIG. 14, as the rod 24 is moved forward distally, the distal portion 56 begins to curve as the rod 24 follows the curve in the channel 42. As shown in FIG. 15, the rod 24 is completely inserted through the bone fastener 22 such that the distal portion 56 is fully curved (e.g., along the cephalad-caudal plane). Due to nitinol's super elastic properties, the rod 24 can be elastically deformed during the procedure and then eventually resume its original shape once in final position. An alternative workflow would proceed by first inserting blank screws 22 and then deploying the nitinol rod 24 through the full length of the in-position screw 22. Once the rod 24 is fully seated through the fastener 22, the instrument 80 may be removed from the proximal end 50 of the rod 24. As shown in FIG. 16, the locking cap 26 may then be secured to the screw head 30 and/or the end 50 of the rod 24, thereby securing their final positions.

Figure 19:
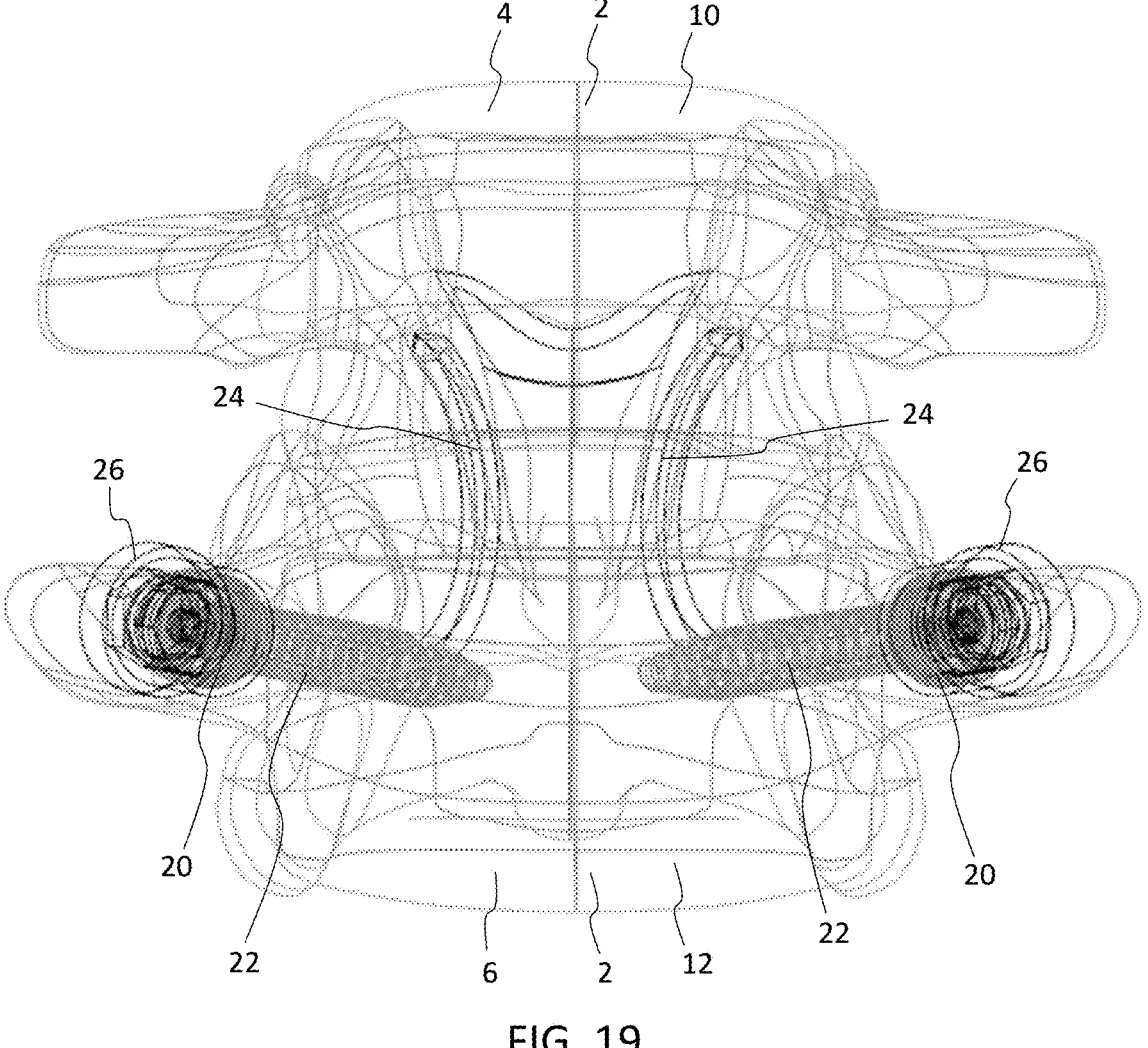
FIG. 19 is a posterior view of two vertebrae with a pair of pedicle-based intradiscal fixation implants implanted through the pedicles of the inferior vertebra and engaged with the vertebral body of the superior vertebra according to one embodiment.
Figure 20:
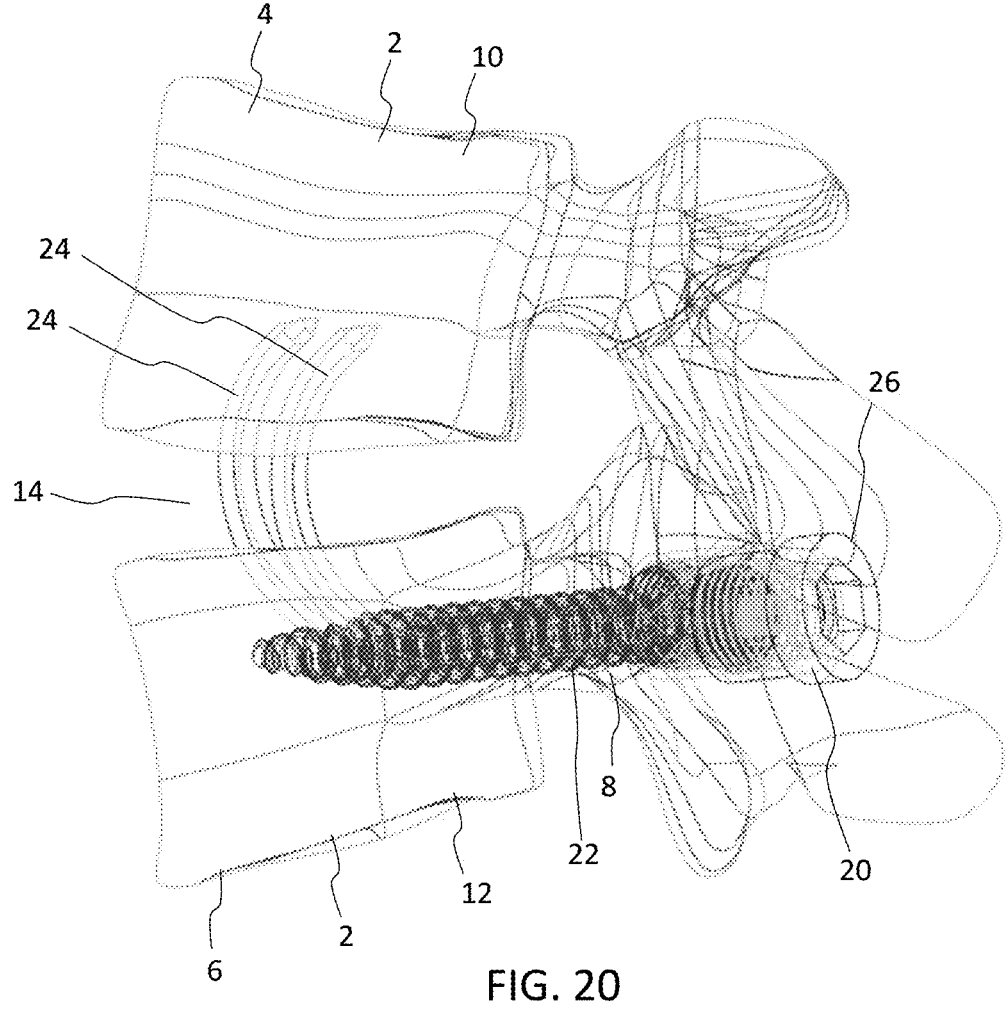
FIG. 20 is a lateral view of two vertebrae and the pair of pedicle-based intradiscal fixation implants shown in FIG. 19.
Figure 21:
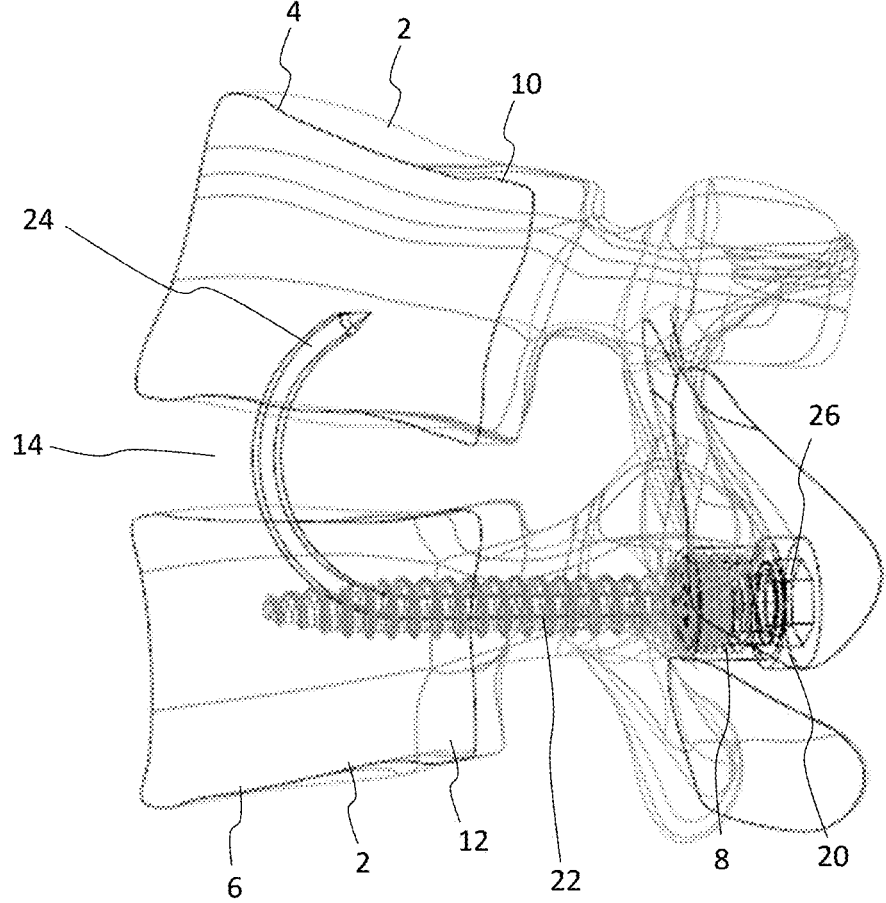
FIG. 21 is a sagittal view of the two vertebrae and the pedicle-based intradiscal fixation implant shown in FIG. 19.

FIGS. 19-21 show an example of the final construct including a pair of bi-pedicle implants 20 deployed through the ipsilateral and contralateral pedicles 8 of the inferior vertebra 6. As shown, each implant 20 is inserted through the respective pedicle 8 of the inferior vertebra 6. The bone fastener 22 is positioned through the pedicle 8 and into the vertebral body 12 of the inferior vertebra 6. The bendable rod 24 extends through the fastener 22 and the distal portion 56 curves upward, thereby allowing for the rod 24 to be secured into the inferior vertebral body 12, through the disc space 14, and into the superior vertebral body 10. The implants 20 may be used in conjunction with an interbody spacer, such as a lumbar interbody fusion device or an expandable implant, which may include a body with lateral legs, for example. The bendable rod 24 may be placed along the inferior pedicle axis and angled accordingly with the axial view to be placed medially to the lateral legs of the interbody while fixating the lower to the upper level. The system may improve access-related morbidity by reducing procedural steps, minimizing soft tissue disruption, and ultimately eliminating violation of the superior facet joint to reduce the risk of adjacent segment disease all while providing improved stability in conjunction with spinal fusion devices.

Figure 22:
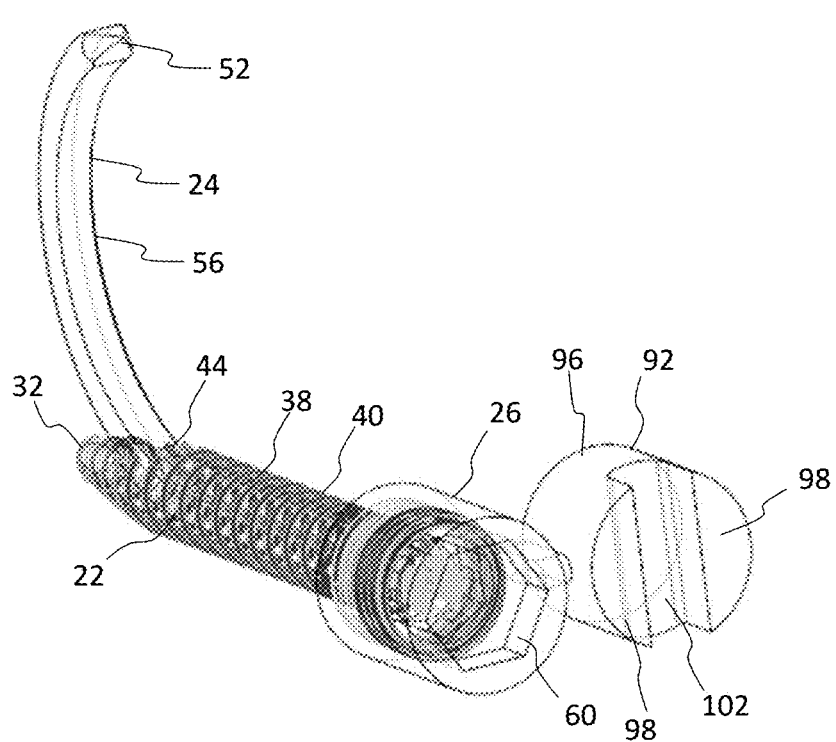
FIG. 22 is a perspective view of a pedicle-based intradiscal fixation device configured for a hybrid case with a modified tulip head according to one embodiment.
Figure 23:
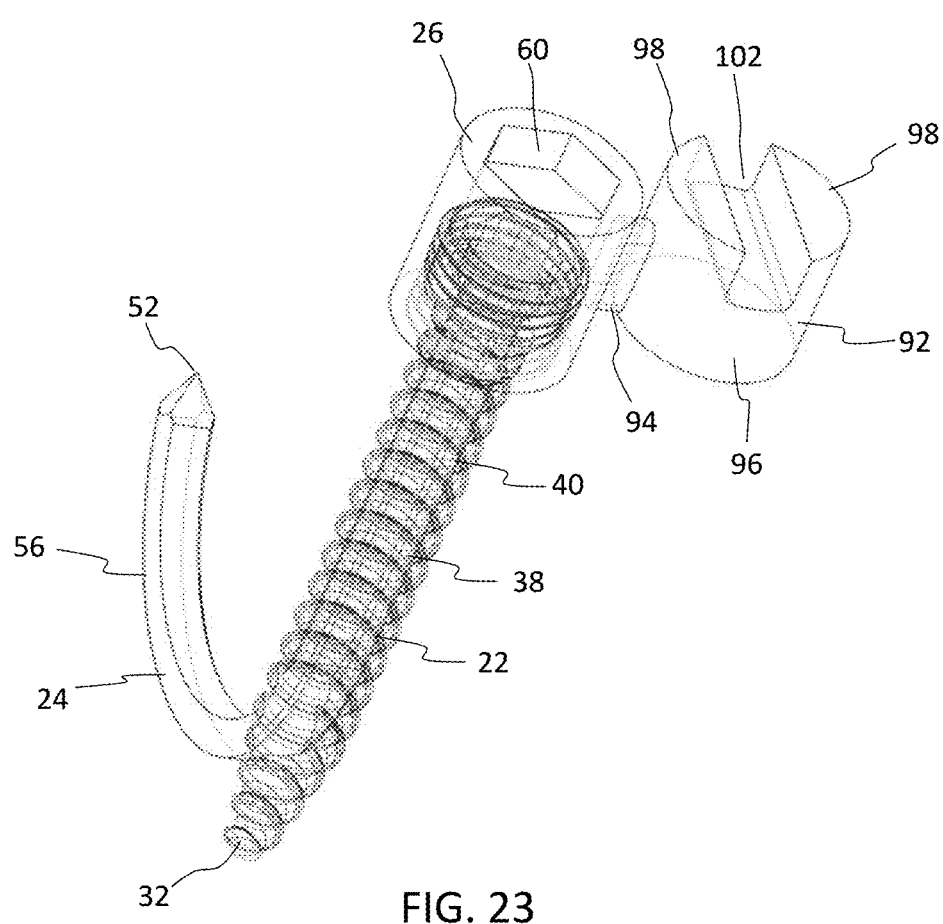
FIG. 23 is an alternative perspective view of the pedicle-based intradiscal fixation device with modified tulip head shown in FIG. 22.
Figure 24:
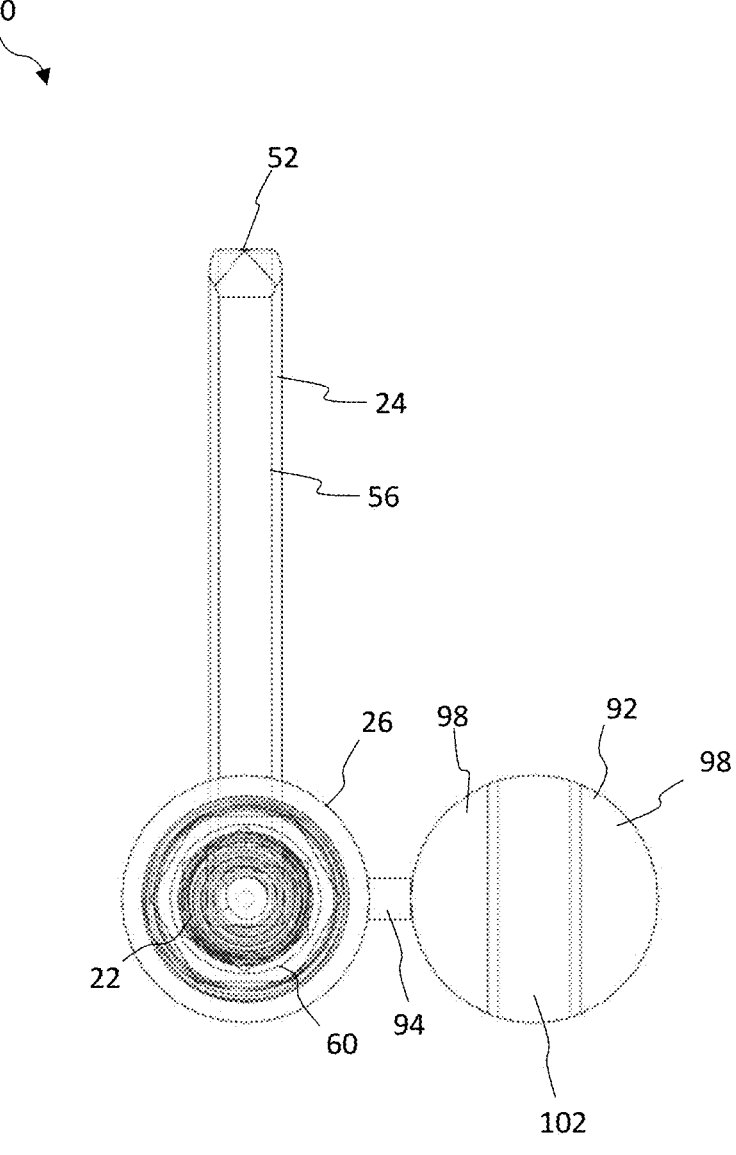
FIG. 24 is a posterior view of the pedicle-based intradiscal fixation device with modified tulip head shown in FIG. 22.

Turning now to FIGS. 22-24, a hybrid implant 90 is shown according to another embodiment. Hybrid implant 90 is similar to implant 20 with a modified tulip head 92 attached to the locking cap 26 to allow for the connection of a spinal rod thereto. In the event of a revision case, proximal threading 58 on the curved nitinol rod 24 as well as the screw head 30 can be engaged and used to perform adequate adjustments. Revision options may vary, for example, based on the patient anatomy, desired outcome, and surgeon preferences. In one embodiment, the revision procedure may include drawing the nitinol rod 24 straight back through the screw 22 and out of the patient, leaving the pedicle screw 22 in place. This allows for a tulip head (not shown) or other compatible instrumentation and implants to incorporate a standard rod fixation system with the existing pedicle screw 22. In another embodiment, the revision procedure may include drawing the nitinol rod 24 into the pedicle screw 22 and then removing the entire assembly completely to open the space to entirely different fixation methods. In yet another embodiment, a hybrid case may be implemented in which implant 20 remains deployed, but modified tulip head 92 is attached to the screw head 30 of the pedicle screw 22 to allow for spinal rods to be inserted therein.

The hybrid implant 90 may include a modified locking cap 26 with tulip head 92 attached thereto. The tulip head 92 may be attached with a rigid arm 94. The arm 94 may be a peg or pin that spans between the locking cap 26 and the tulip head 92. It will be appreciated that the tulip head 92 may be integrally formed with the locking cap 26 or otherwise suitably connected thereto. The tulip head 92 may be offset laterally to one side of the locking cap 26. The tulip head 92 may extend from an upper surface or top to a lower surface or bottom. The tulip head 92 may include a body 96 and a pair of arms 98 that extend upwardly from the body 96. The opposed arms 98 may define a channel or rod slot 102 therebetween. The rod slot 102 may be sized and configured to accept a suitable spinal rod. The spinal rod may be secured in the rod slot 102, for example, via a threaded or non-threaded locking cap (not shown). As shown in FIG. 24, the rod slot 102 may be aligned substantially parallel to the body of the rod 24, although it will be appreciated that the rod slot 102 may be oriented or aligned in any suitable configuration for the desired rod construct. It will further be appreciated that the tulip head 92 could be modified to replace the locking cap 26 or the arrangement could be otherwise configured to allow for connection to a spinal rod and/or other fixation devices.

Iatrogenic adjacent segment disease and other surgical issues have been attributed to pedicle screw fixation previously. This intradiscal fixation devices and methods described herein may obviate the need for pedicle screw fixation while potentially avoiding their iatrogenic effects. Traditional techniques may require multiple incisions for even minimally invasive pedicle screw fixation. Intradiscal fixation rods conjoined to full-length pedicle screws allow for this fixation method to accomplish a major clinical goal of avoiding violation of the superior facet joint while still securely capturing both the inferior and superior vertebral bodies. The workflow can be performed from a minimally invasive posterior approach, reducing procedural steps compared to other posterior approaches and avoiding potential disruption of vasculature or nerve roots found in anterior/lateral approaches. The pedicle-based intradiscal fixation devices described herein may provide better stability in flexion, extension, and/or axial rotation compared with other anchor type fixation methods. The construct accommodates the potential need to perform a range of revisions. The system may have numerous applications due to its unique geometry and improved biocompatibility.

It will be further understood that various changes in the details, materials, and arrangements of the parts which have been described and illustrated in order to explain the nature of this invention may be made by those skilled in the art without departing from the scope of the invention as expressed in the claims. One skilled in the art will appreciate that the embodiments discussed above are non-limiting. It will also be appreciated that one or more features of one embodiment may be partially or fully incorporated into one or more other embodiments described herein.

What is claimed is:

1. A pedicle-based intradiscal implant comprising:
a bendable rod that extends from a proximal end having an outer threaded portion to a distal end configured to engage bone;
a bone fastener having a threaded screw head and a cannula extending along a central longitudinal axis configured to receive the bendable rod; and a locking cap with an internally threaded seat for engaging with the screw head of the bone fastener and a central protrusion defining a cavity for receiving the proximal end of the bendable rod.

2. The intradiscal implant of claim 1, wherein the locking cap has a cylindrical body defining a drive recess opposite to the internally threaded seat.

3. The intradiscal implant of claim 1, wherein the cavity in the central protrusion of the locking cap is non-threaded and is configured to push the rod forward, thereby compressing the rod securely.

4. The intradiscal implant of claim 1, wherein the cavity in the central protrusion of the locking cap is threaded and is configured to mate with the outer threaded portion of the bendable rod, thereby pulling the rod backward to secure the rod.

5. The intradiscal implant of claim 1, wherein a portion of the cannula is a curved portion located near the distal end of the bone fastener.

6. The intradiscal implant of claim 1, wherein the bendable rod is flexible such that the rod has a straight configuration and is bendable into a curved configuration.

7. The intradiscal implant of claim 6, wherein in the curved configuration, the bendable rod has a straight portion and a curved portion where the rod is curved in an arc up to 180°.

8. The intradiscal implant of claim 1, wherein the bendable rod is formed of a shape-memory material.

9. The intradiscal implant of claim 8, wherein the bendable rod is formed of nitinol.

10. The intradiscal implant of claim 1, wherein a distal portion of the bendable rod has a polygonal cross-section with planar faces and a proximal portion of the bendable rod has a cylindrical shape.

11. The intradiscal implant of claim 1, wherein the bone fastener is a pedicle screw with a proximal end including a recess configured to receive an instrument for inserting the pedicle screw and a distal end with a tip configured to be inserted into the pedicle of an inferior vertebra.

12. A hybrid implant comprising:
a bendable rod configured to engage bone;
a bone fastener having a threaded screw head and a cannula extending along a central longitudinal axis configured to receive the bendable rod;
a locking cap with an internal seat for engaging with the screw head of the bone fastener and a central protrusion defining a cavity for receiving one end of the bendable rod; and
a tulip head coupled to the locking cap, the tulip head having a body with a pair of opposed arms defining a rod slot sized and configured to accept a spinal rod.

13. The implant of claim 12, wherein the tulip head is integrally coupled to the locking cap with a rigid arm.

14. The implant of claim 12, wherein the tulip head is offset laterally to the locking cap.

15. The implant of claim 12, wherein the rod slot of the tulip head is aligned in parallel to the bendable rod.

16. The implant of claim 12, wherein the screw head is externally threaded and the internal seat of the locking cap is internally threaded to thereby threadedly interface with the screw head.

17. The intradiscal implant of claim 12, wherein a portion of the cannula is a curved portion located near the distal end of the bone fastener.

18. The intradiscal implant of claim 12, wherein the bendable rod is flexible such that the rod has a straight configuration and is bendable into a curved configuration.

19. The intradiscal implant of claim 18, wherein in the curved configuration, the bendable rod has a straight portion and a curved portion where the rod is curved in an arc up to 180°.

20. The intradiscal implant of claim 12, wherein the bendable rod is formed of a shape-memory material.

\* \* \* \* \*